United States Patent [19]

Detty et al.

[11] 4,434,098
[45] Feb. 28, 1984

[54] SUBSTITUTED BENZOTELLUROPYRONES

[75] Inventors: Michael R. Detty; Bruce J. Murray; Jerome H. Perlstein, all of Rochester, N.Y.

[73] Assignee: Eastman Kodak Company, Rochester, N.Y.

[21] Appl. No.: 279,300

[22] Filed: Jul. 1, 1981

[51] Int. Cl.$^3$ ............................................. C07D 345/00
[52] U.S. Cl. .................................................. 260/239 R
[58] Field of Search ...................................... 260/239 R

[56] References Cited

PUBLICATIONS

N. Dereu & M. Renson, Ph.D. Thesis, University, Liege, Belgium, Journal of Organometallic Chemistry, vol. 208, pp. 11–21, 1981.
N. Dereu & M. Renson, Phosphorous and Sulfur, vol. 6, p. 73, 1979.
W. Lohner & K. Praefcke, Chem.-Ztg., vol. 103, p. 265, 1979.
J.-L. Piette & M. Renson, Bull. Soc. Chim. Belges, vol. 80, p. 669, 1971.
J.-L. Piette, P. Thibaur & M. Renson, Tetrahedron, vol. 34, p. 655, 1978.
W. Lohner & K. Praefcke, Journal of Organometallic Chemistry, vol. 208, pp. 39–42, 1981., Primary Examiner—Paul M. Coughlan, Jr.
Assistant Examiner—D. B. Springer
Attorney, Agent, or Firm—John R. Everett

[57] ABSTRACT

The present invention discloses novel substituted benzotelluropyrones and a novel method for making such compositions. The compositions are useful as intermediates for making benzotelluropyrylium and benzotelluropyrylium diketonate electron dye sensitizers for electron donating photoconductive compositions and elements.

5 Claims, No Drawings

SUBSTITUTED BENZOTELLUROPYRONES

FIELD OF THE INVENTION

This invention relates to novel benzotelluropyrone compositions of matter, including benzotelluropyrone thiones, a novel method for making such compositions and their utility as intermediates in preparing benzotelluropyrylium and benzotelluropyrylium diketonate electron accepting dye sensitizers for electron donating photoconductive compositions and elements.

BACKGROUND OF THE INVENTION

A great number of chalcogen-containing organic compositions of matter are known. Telluroflavanone has been prepared. Benzotelluropyrone, 2-methyl benzotelluropyrone and telluroxanthone have also been prepared. See *Phosphorous and Sulfur* by Dereu et al, Vol. 6, page 73 (1979). However, a range of substituted benzotelluropyrone compositions of matter, including benzotelluropyrone thiones, have not been heretofore available. As far as can be determined, no method has been available for making such compounds.

SUMMARY OF THE INVENTION

The present invention provides a novel method for making novel benzotelluropyrone compositions of matter, including benzotelluropyrone thiones. The compositions are useful as intermediates in the preparation of novel benzotelluropyrylium dyes. The latter dyes have many uses such as sensitizers for photoconductive compositions.

The novel method of our invention comprises the step of:

cyclizing a 3-aryltelluroacrylic acid or a 3-aryltelluroacryloyl halide; wherein the 3-aryl group has at least one electron donating substituent in a meta position relative to the telluro group. For the purpose of the invention described herein, the term "3-aryltelluroacrylic acid" includes 3-aryltellurothioacrylic acid and 3-aryltelluroselenoacrylic acid and their acid ester derivatives. The term "3-aryltelluroacryloyl halide" includes 3-aryltellurothioacryloyl halide and 3-aryltelluroselenoacryloyl halide.

If desired the thus formed benzotelluropyrone is isolated using any technique for separating and purifying chemical compositions of matter.

PREFERRED EMBODIMENTS

In a preferred embodiment, the substituted benzotelluropyrone compositions of matter, including substituted benzotelluropyrone thiones, of the present invention are prepared by a method comprising the steps of:

cyclizing a 3-aryltelluroacrylic acid or a 3-aryltelluroacryloyl halide, wherein (a) the aryltelluroacrylic acid or 3-aryltelluroacryloyl halide has the structure:

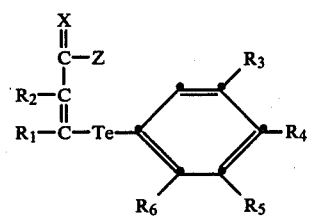

(I)

and (b) the resulting substituted benzotelluropyrone has the structure:

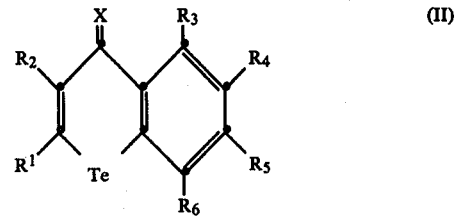

(II)

in which structures, $R_1$, and $R_2$ each independently represents hydrogen, alkyl, alkoxy, halogen or aryl, or together with the carbon atoms to which they are attached form a mono- or polycyclic, carbocyclic or heterocyclic fused ring structure having about 5 to 20 carbon atoms;

$R_3$ and $R_5$ each independently represents an electron donating group, hydrogen, halogen, alkyl or aryl, provided that at least one of $R_3$ and $R_5$ is an electron donating group;

$R_4$ and $R_6$ each independently represents hydrogen, halogen or alkyl; or $R_4$ and $R_5$, or $R_5$ and $R_6$ together with the carbon atoms to which they are attached form a mono- or polycyclic, carbocyclic or heterocyclic fused ring structure having 5 to 20 carbon atoms;

X represents O, S or Se; and

Z represents OH, Br, Cl or I.

The novel substituted benzotelluropyrone compositions represented by Structure II can be converted to other novel substituted benzotelluropyrone compositions of matter in which the electron donor substituents on the 3-aryl group are replaced. Thus, the novel benzotelluropyrones provided by the present invention are substituted with at least one substituent other than a 2-methyl. The present invention includes all substituted benzotelluropyrones with the exception of 2-methyl-benzotelluropyrone.

Preferred substituted benzotelluropyrones have the structure:

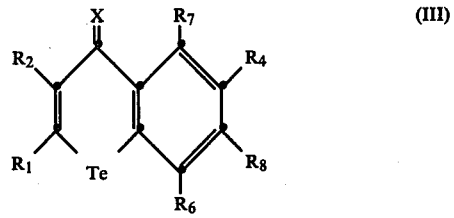

(III)

$R_1$ and $R_2$ each independently represents hydrogen, alkyl, alkoxy, halogen or aryl, or together with the carbon atoms to which they are attached form a mono- or polycyclic, carbocyclic or heterocyclic fused ring structure having about 5 to 20 carbon atoms;

$R_7$ and $R_8$ each independently represents an electron donating group, hydrogen, alkyl or aryl;

$R_4$ represents hydrogen, halogen or alkyl; or $R_4$ and $R_7$, or $R_4$ and $R_8$, together with the carbon atoms to which they are attached, form a mono- or polycyclic, substituted carbocyclic or heterocyclic fused ring structure having about 5 to 20 carbon atoms;

$R_6$ represents hydrogen, halogen or alkyl; or $R_6$ and $R_8$, together with the carbon atoms to which they are attached, form a mono- or polycyclic, carbocyclic or heterocyclic fused ring structure having about 5 to 20 carbon atoms;

provided that when $R_1$ is methyl, at least one of $R_2$, $R_4$, $R_6$, $R_7$ and $R_8$ is other than hydrogen.

Heterocyclic fused rings include rings having hetero atoms such as O, N, S, Se or Te. Examples of the latter groups include the groups generally used to form cyanine dyes, such as pyridyl, furaryl, thiophenyl, selenophenyl, tellurophenyl, oxazolyl, thiazolyl, selenazolyl, tellurazolyl, benzoxazolyl, benzthiazolyl, benzselenazolyl, and benztellurazolyl. "Alkyl" and alkoxy refer to a branched- or straight-chain hydrocarbon having up to 16 carbon atoms, such as methyl, butyl, dodecyl, nonyl or isobutyl; "aryl" includes phenyl, naphthyl and anthryl. The carbocyclic and heterocyclic fused rings, alkyl and aryl are optionally further substituted with substituents such as allyl, aryl, halogen, nitro, cyano, carboxy, hydroxy, alkoxy, aryloxy, aralkyl, acyl, amide sulfonamide, dialkylamine or amino. Electron donating groups include hydroxy, alkoxy, aryloxy, amino, dialkylamino, alkylazo, arylazo, halogen, alkylthio and arylthio.

DETAILED PRESENTATION OF THE INVENTION

A possible theory of why the method of the present invention works is presented to clarify the invention. However, such theory should not be construed in any way as limiting the invention.

Z-3-aryltelluroacrylic acids or their derivatives, in the presence of strong acids or Friedel-Crafts catalysts, form an acylium ion (IV) which can experience electrophilic attack at two positions on the aryltelluro aromatic ring as shown in the scheme below. Attack on the carbon bearing tellurium (ipso acylation) leads to aryl migration (V), and not to benzotelluropyrone formation (II). Attack at either carbon adjacent to the one bearing tellurium (ortho acylation) leads to the desired benzotelluropyrone products.

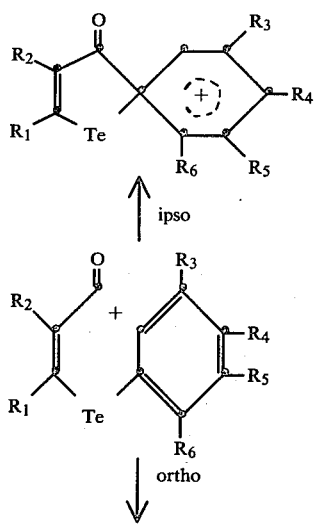

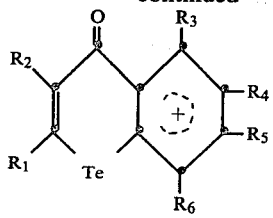

Although all aryl oxygen and aryl sulfur acrylic acid derivatives and some aryl selenium acrylic acid derivatives undergo only ortho acylation, the aryl telluro acrylic acid derivatives only undergo ipso acylation unless an electron donating substituent is in one or both meta positions in the aryl ring. Furthermore, these substituents must be $\sigma^+$ ortho-para activators and meta-deactivators. Thus, methoxy and fluoro substituents in the meta position result in benzotelluropyrones while methyl in the meta position does not.

The 3-aryltelluroacrylic acid starting materials used for making the compounds of this invention are readily prepared according to the procedure described by Wadsworth and Detty, *J. Org. Chem.*, 1980, 45, 4611.

The 3-aryltelluroacryloyl halide materials are prepared from the 3-aryltelluroacrylic acids by classical methods such as oxalyl chloride or thionyl chloride acting on the acid.

According to one aspect of the present invention, the starting materials are cyclized by contact with a Friedel-Crafts catalyst in a halogenated solvent such as methylene chloride, preferably in an inert atmosphere. The temperature of the solution is maintained at or below 0° C. From 0.1 to 1.1 equivalents of the selected Friedel-Crafts catalyst are added to the solution. The temperature of the solution is raised to about 20° C. to 40° C. to allow the reaction to proceed to formation of the novel benzotelluropyrone compositions of matter, including benzotelluropyrone thiones. After the reaction is completed, the reaction mixture is cooled to room temperature.

Useful Friedel-Crafts catalysts include aluminum chloride ($AlCl_3$), aluminum bromide ($AlBr_3$), zinc chloride ($ZnCl_2$), zinc bromide ($ZnBr_2$) or sodium tetrachloroaluminate ($NaAlCl_4$). Aluminum chloride is the preferred catalyst.

According to another aspect of the present invention, the starting materials are cyclized by contact with a solution of phosphorous pentoxide in methane sulfonic acid. The contact is carried out by adding a solution consisting of from about 5.0 to 10.0 percent by weight of phosphorous pentoxide in methane sulfonic acid, to 0.1 to 0.5 molar equivalents of the starting materials.

The novel substituted benzotelluropyrone compositions of matter, including substituted benzotelluropyrone thiones, are, if desired, isolated from the reaction mixture and purified using any chemical separation method and technique for isolating and purifying chemical compounds. Known methods and techniques include, for example, soaking the crude reaction mixture with cold water, removing the product by extraction with a water-immiscible solvent such as a halogenated solvent, drying, precipitation by concentration, and recrystallization from an organic solvent such as methanol when the products are solids, or separating chromatographically when the products are liquids.

The novel method of this invention was carried out for the preparation of substituted benzotelluropyrone compositions of matter, including benzotelluropyrone thiones. The following examples illustrate the method of this invention:

EXAMPLE 1

Preparation of 4H-7-methoxy-2-phenylbenzo[b]telluropyrone

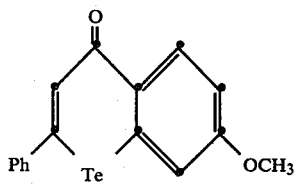

Procedure A

Z-3-(3-methoxyphenyltelluro)cinnamoyl chloride (0.50 g, 1.3 mmol) was dissolved in 5 ml of methylene chloride under an argon atmosphere. The resulting solution was cooled to −78° C. and 0.50 g of aluminum chloride was added. The reaction mixture immediately turned dark red. The cooling bath was removed. When the reaction mixture reached ambient temperature, the reaction mixture was poured into ice water. The products were extracted with methylene chloride. The combined extracts were dried over sodium sulfate and concentrated. Careful chromatography on silica gel eluting with 10/7/3 methylene chloride/hexane/ethyl acetate followed by recrystallization from methanol gave 0.27 g (60%) of a yellow solid, mp 118°–119.5° C.

Procedure B

Phosphorous pentoxide (1 g) was dissolved in 8 ml of methanesulfonic acid. To this solution was added Z-3-(3-methoxyphenyltelluro)cinnamic acid (0.480 g, 1.25 mmol). The resulting dark red mixture was stirred overnight at room temperature. The reaction mixture was added dropwise to 200 ml of saturated sodium bicarbonate. The products were extracted with methylene chloride (3×50 ml). The combined extracts were dried over sodium sulfate and concentrated. Recrystallization from methanol gave 0.28 g (62%) of a yellow solid, having a melting point of 118°–119.5° C.

EXAMPLE 2

Preparation of 4H-5,7-dimethoxy-2-phenylbenzo[b]telluropyrone

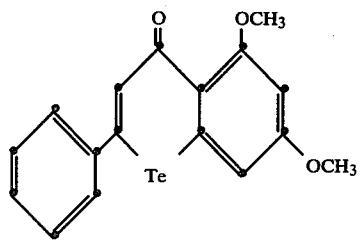

Procedure A

Z-3-(3,5-dimethoxyphenyltelluro)cinnamic acid (2.60 g, 6.33 mmol) was added to 10 ml of oxalyl chloride. The resulting mixture was stirred 0.5 h at 40° C. and was then concentrated in vacuo. The residue was taken up in 20 ml of methylene chloride and the resulting solution was cooled to 0° C. under an argon atmosphere. Aluninum chloride (0.85 g, 6.39 mmol) was added giving a dark red solution. The cooling bath was removed and the reaction mixture was poured into ice water. The products were extracted with methylene chloride. The extract was dried over sodium sulfate and concentrated. Chromatography on silica gel eluting with 10% acetone-methylene chloride gave 2.23 g (90%) of a yellow solid, having a melting point of 98°–100° C.

Procedure B

Phosphorous pentoxide (1 g) was dissolved in 10 ml of methanesulfonic acid. Z-3-(3,5-dimethoxyphenyltelluro)cinnamic acid was added. The resulting mixture was stirred at ambient temperature for 3.0 hours. The reaction mixture was then added dropwise to 200 ml of saturated sodium bicarbonate solution. The products were extracted with methylene chloride. The extracts were dried over sodium sulfate and concentrated. The residue was recrystallized from 3/1 ether/methylene chloride to give 0.15 g (38%) of a yellow solid, having a melting point of 98°–100° C.

EXAMPLE 3

Preparation of 4H-7-fluoro-2-phenylbenzo[b]telluropyrone

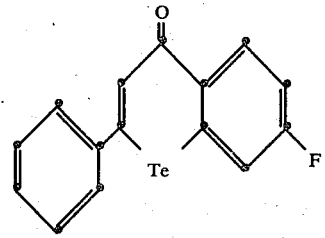

Procedure A

Z-3-(3-fluorophenyltelluro)cinnamic acid (6.50 g, 0.0176 mol) was added to 20 ml of oxalyl chloride under argon. The resulting mixture was stirred for 0.5 hours at 50° C. The reaction mixture was concentrated in a vacuum. The residue was dissolved in 25 ml of methylene chloride. The resulting solution was cooled to 0° C. and aluminum chloride (2.7 g, 0.020 mol) was added. The cooling bath was removed. When the reaction warmed to ambient temperature, the reaction mixture was poured into ice water. The products were extracted with methylene chloride.

The combined extracts were dried over sodium sulfate and concentrated to give a red crystalline residue. Recrystallization from methanol gave 5.30 g (82%) of a red solid that was not the desired benzotelluropyrone. The mother liquors were concentrated. Chromatography of the residue on silica gel eluting with 5% acetone-methylene chloride gave 0.30 g (4.9%) of yellow-needles, having a melting point of 138.5°–139.5° C.

EXAMPLE 4

Preparation of 4H-7-methoxybenzo[b]telluropyrone

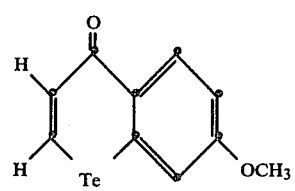

Procedure A

Z-3-(3-methoxyphenyltelluro)acrylic acid (1.20 g, 3.92 mmol) was added to 5 ml of oxalyl chloride. The resulting mixture was warmed at 40° C. under argon until gas evolution stopped. After stirring an additional 0.5 hours at room temperature, the reaction mixture was concentrated in vaccuo. The residue was taken up in 20 ml of methylene chloride and cooled to 0° C. Aluminum chloride (0.50 g, 3.8 mmol) was added and the cooling bath was removed. After warming to ambient temperature, the reaction mixture was poured into ice water and the products were extracted with methylene chloride (2×50 ml). The combined extracts were dried over sodium sulfate and concentrated. Careful chromatography on silica gel eluting with 10% acetone-methylene chloride, followed by recrystallization gave 0.75 g of a yellow, crystalline solid, having a melting point of 102°–103° C.

EXAMPLE 5

Preparation of 4H-5,7-dimethoxy-2-methylbenzo[b]telluropyrone

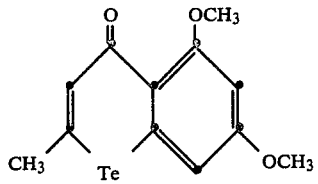

Procedure A

Z-3-(3,5-dimethoxyphenyltelluro)but-2-enoic acid (2.25 g, 6.45 mmol) was added to 10 ml of oxalyl chloride. The resulting mixture was stirred under an argon atmosphere for 1 hour. The reaction mixture was concentrated in vaccuo. The residue was taken up in 20 ml of methylene chloride and cooled to 0° C. Aluminum chloride (1.33 g, 10.0 mmol) was added giving a dark red solution. The cooling bath was removed. Upon reaching ambient temperature, the reaction mixture was poured into 100 ml of ice water. The products were extracted with methylene chloride (3×50 ml). The combined extracts were dried over sodium sulfate and concentrated. Chromatography on silica gel eluting with 30% acetonemethylene chloride and recrystallization from methanol gave 1.31 g (62%) of a tan powder, having a melting point of 127.5°–129° C.

The structure of each compound prepared in the above examples was confirmed by melting points, NMR analysis, infrared spectral analysis, mass spectral analysis and elemental analysis.

A representative portion of compounds which can be made by the method of the invention are presented in Table I wherein Ph represents phenyl.

TABLE I

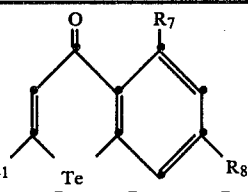

| Compound No. | $R_1$ | $R_7$ | $R_8$ |
|---|---|---|---|
| 1 | Ph | H | $CH_3O$ |
| 2 | $CH_3$ | H | $CH_3O$ |
| 3 | H | H | $CH_3O$ |
| 4 | Ph | $CH_3O$ | H |
| 5 | $CH_3$ | $CH_3O$ | H |
| 6 | H | $CH_3O$ | H |
| 7 | Ph | F | H |
| 8 | $CH_3$ | F | H |
| 9 | H | F | H |
| 10 | Ph | H | F |
| 11 | $CH_3$ | H | F |
| 12 | H | H | F |
| 13 | Ph | $CH_3O$ | $CH_3O$ |
| 14 | $CH_3$ | $CH_3O$ | $CH_3O$ |
| 15 | H | $CH_3O$ | $CH_3O$ |
| 16 | Ph | HO | H |
| 17 | $CH_3$ | HO | H |
| 18 | H | HO | H |
| 19 | Ph | H | $CH_3CH_2CH_2O$ |
| 20 | $CH_3$ | H | $CH_3CH_2CH_2O$ |
| 21 | H | H | $CH_3CH_2CH_2O$ |
| 22 | Ph | H | $CH_3O$ |
| 23 | $CH_3$ | H | $CH_3O$ |
| 24 | H | H | $CH_3O$ |
| 25 | Ph | $CH_3O$ | $CH_3O$ |
| 26 | $CH_3$ | $CH_3O$ | $CH_3O$ |
| 27 | H | $CH_3O$ | $CH_3O$ |

Representative compounds having fused carbocyclic substituents on the benzotelluropyrone nucleus include:
- 6H-3-methoxy dibenzo[b]telluropyrone;
- 6H-3-methoxy dibenzo[b]telluropyrone;
- 6H-10-aza-3-methoxy dibenzo[b]telluropyrone and
- 6H-7-aza-3-methoxy dibenzo[b]telluropyrone.

The benzotelluropyrone compositions of matter are optionally converted to the corresponding thiones using techniques disclosed by Pederson, Scheibye, Nilsson, and Lawesson in *Bull. Soc. Chim. Belg.*, 1978, 87, 223. One method involves contacting benzotelluropyrone compositions of matter with the sulfurating species

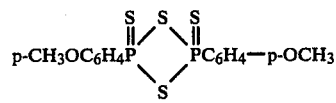

obtained from the reaction between phosphorous pentasulfide and anisole. This procedure is illustrated in Example 6.

EXAMPLE 6

Preparation of 4H-7-methoxy-2-phenylbenzo[b]telluropyrone thione

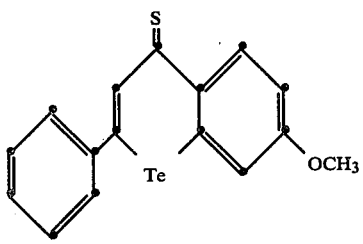

The sulfurating species

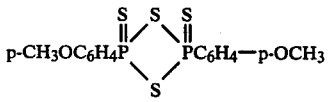

obtained from phosphorous pentasulfide and anisole (3.61 g, 0.0089 mmol) was dissolved in 360 ml of hot toluene in a beaker open to the air. The telluroflavone (3.00 g, 0.00824 mol) was dissolved in toluene (40 ml). The two solutions were mixed hot. After one minute at reflux, the reaction mixture was concentrated. The residue was eluted through a Florisil column with methylene chloride. Recrystallization from toluene gave 1.67 g (53%) of green crystals, mp 136.5°–138.5° C.

Methods for converting the electron donating groups represented by $R_3$ and $R_5$ on Structure II to other groups represented by $R_7$ and $R_8$ in Structure III include known methods including reduction of halogen and thio groups, hydrolysis of ether groups, and oxidation of amino groups.

The benzotelluropyrones of this invention are useful intermediates for preparing benzotelluropyryliums, benzotelluropyrylium boron diketonates and benzotelluropyrylium phosphorous tetrafluoride diketonates. Benzotelluropyrones are converted to pyrylium type dyes by using any of the well-known methods for converting pyrones to pyrylium dyes.

The latter benzotelluropyrylium compounds are dyes. As such, they have many uses. Novel benzotelluropyrylium sensitizing dyes for photoconductive compositions are disclosed in commonly assigned U.S. patent application Ser. No. 279,365, now U.S. Pat. No. 4,365,017 granted Dec. 21, 1982, entitled "Telluropyrylium Electron Accepting Dye Sensitizers For Electron Donating Photoconductive Compositions" and U.S. patent application Ser. No. 279,363, now U.S. Pat. No. 4,365,016 granted Dec. 21, 1982, entitled "Benzotelluropyrylium Diketonate Electron Accepting Dye Sensitizers For Electron Donating Photoconductive Compositions." Both applications, in the name of Detty et al, were filed on the same date as the present case.

The invention has been described in detail with particular reference to preferred embodiments thereof, but it will be understood that variations and modifications can be effected within the spirit and scope of the invention.

We claim:

1. A substituted benzotelluropyrone compound having at least one substituent other than a 2-methyl.

2. A substituted benzotelluropyrone compound having the structure:

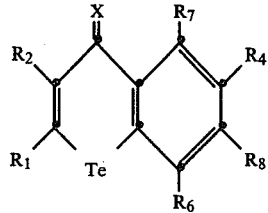

(III)

wherein, $R_1$ and $R_2$ each independently represents hydrogen, alkyl, alkoxy, halogen or aryl, or together with the carbon atoms to which they are attached form a mono- or polycyclic, carbocyclic fused ring structure having 5 to 20 carbon atoms;

$R_7$ and $R_8$ each independently represents an electron donating group, hydrogen, alkyl or aryl;

$R_4$ and $R_6$ each independently represents hydrogen, halogen or alkyl; or $R_4$ and $R_7$, or $R_4$ and $R_8$, together with the carbon atoms to which they are attached, form a mono- or polycyclic, carbocyclic fused ring structure having 5 to 20 carbon atoms; or $R_6$ and $R_8$, together with the carbon atoms to which they are attached, form a mono- or polycyclic, carbocyclic fused ring structure having 5 to 20 carbon atoms;

X represents O, S or Se;

provided that when $R_1$ is methyl, at least one of $R_2$, $R_4$, $R_6$, $R_7$ and $R_8$ is other than hydrogen.

3. A compound as in claim 2 wherein $R_1$, $R_2$, $R_3$, $R_4$, $R_6$, $R_7$ and $R_8$ represent hydrogen, methoxy, phenyl, methyl or fluorine.

4. A compound of matter as in claim 2 wherein at least one of $R_7$ and $R_8$ is an electron donating group.

5. A compound of matter as in claim 2 selected from the group consisting of:
4H-7-methoxy-2-phenylbenzo[b]telluropyrone;
4H-5,7-dimethoxy-2-phenylbenzo[b]telluropyrone;
4H-7-fluoro-2-phenylbenzo[b]telluropyrone;
4H-7-methoxybenzo[b]telluropyrone;
4H-5,7-dimethoxy-2-methylbenzo[b]telluropyrone or
4H-7-methoxy-2-phenylbenzo[b]telluropyrone thione.

* * * * *